(12) United States Patent
Khan et al.

(10) Patent No.: US 7,344,587 B2
(45) Date of Patent: Mar. 18, 2008

(54) MAGNETIC INK TISSUE MARKINGS

(75) Inventors: Misbah H. Khan, Newport Beach, CA (US); Richard Rox Anderson, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 323 days.

(21) Appl. No.: 10/913,114

(22) Filed: Aug. 6, 2004

(65) Prior Publication Data

US 2005/0061198 A1 Mar. 24, 2005

Related U.S. Application Data

(60) Provisional application No. 60/493,230, filed on Aug. 6, 2003.

(51) Int. Cl.
*A61K 6/00* (2006.01)
*C09D 11/00* (2006.01)

(52) U.S. Cl. ............... 106/31.64; 106/31.32; 8/404; 252/62.51 R; 252/62.56; 252/62.54; 128/898; 128/899; 600/12

(58) Field of Classification Search ............ 106/31.64, 106/31.32; 252/62.51 R, 62.56, 62.54; 8/404
See application file for complete search history.

(56) References Cited

U.S. PATENT DOCUMENTS 4,665,912 A * 5/1987 Burton ............... 606/185
6,013,122 A * 1/2000 Klitzman et al. ........ 106/31.03
6,192,890 B1 * 2/2001 Levy et al. ............... 128/899
6,800,122 B2 * 10/2004 Anderson et al. ........ 106/31.03
6,814,760 B2 * 11/2004 Anderson et al. ............ 8/404
6,881,249 B2 * 4/2005 Anderson et al. ........ 106/31.03

OTHER PUBLICATIONS

Huzaira et al, "Magnetite Tattoos", Lasers in Surgery and Medicine 31:121-128, Aug. 6, 2002.*
Anderson et al., "Selective photothermolysis: precise microsurgery by selective absorption of pulsed radiation," *Science*, 220:524-527 (1983).
Anderson, "Tattooing should be regulated," *N. Engl. J. Med.*, 326(3):207 (1992).
Apfelberg et al., "Argon laser treatment of decorative tattoos," *Br. J. Plast. Surg.*, 32:141-144 (1979).
Apfelberg et al., "Comparison of argon and carbon dioxide laser treatment of decorative tattoos: a preliminary report," *Ann. Plast. Surg.*, 14:6-15 (1985).
Bailin et al., "Removal of tattoos by $CO_2$ laser," *J. Dermatol. Surg. Oncol.*, 6(12):997-1001 (1980).
Barnzenen, "Magnetic tattoo," www.halfbakery.com/idea/Magnetic_20Tattoo, Post Date Nov. 1, 2002 (Redacted).
Bjornberg, "Reactions to light in yellow tattoos from cadmium sulfide," *Arch. Dermatol.*, 88:83-87 (1963).
Ferguson et. al., "The Q-switched neodymium: YAG laser and tattoos: a microscopic analysis of laser-tattoo interactions," *Br. J. Dermatol.*, 137(3):405-410 (1997).

(Continued)

*Primary Examiner*—C. Melissa Koslow
(74) *Attorney, Agent, or Firm*—Fish & Richardson P.C.

(57) ABSTRACT

The invention provides tissue markings (such as tattoos) comprising magnetic particles, e.g., magnetite, and methods for making and altering, e.g., removing them.

33 Claims, 6 Drawing Sheets

Magnetic particles (24) moved into upper dermis and/or epidermis and/or removed from skin

OTHER PUBLICATIONS

Fitzpatrick et al., "Tattoo removal using the alexandrite laser," *Arch. Dermatol.* 130:1508-1514 (1994).

Goldman et al., "Radiation from a Q-switched ruby laser," *Journ. Invest. Dermatol.*, 44:69-71 (1965).

Goldman et. al., "Laser treatment of tattoos," *JAMA* 201(11):163-166 (1967).

Goldstein, "Histologic reactions in tattoos," *J. Dermatol. Surg. Oncol,.* 5(11):896-900 (1979).

Grumet, "Psychodynamic implications of tattoos," *Amer. J. Orthopsychiat.*, 53(3):482-492 (1983).

Helmenstine, "Tattoo Ink Chemistry," chemistry.about.com/library/weekly/aa121602a.htm, posted Dec. 16, 2002.

Helmenstine, "Q. Can a Tattoo React with Magnetic Resonance Imaging (MRI)?" chemistry.about.com/cs/howthingswork/f/bltattoomri.htm, printed Aug. 6, 2004, post date unknown.

Hudson, "Tattoos and MRI Scans," www.tattoo.about.com/cs/tatfaq/a/mri_scan.htm, posted Feb. 22, 2004.

Huzaira et al., "Magnetite tattoos," *Lasers Surg Med.*, 31:121-128 (2002).

Kiistala, "Suction blister device for separation of viable epidermis from dermis," *J Invest Dermatol.*, 50(2):129-137 (1968).

Kilmer et al., "Clinical use of the Q-switched ruby and the Q-switched Nd:YAG (1064 nm and 532 nm) lasers for treatment of tattoos," *J. Dermatol. Surg. Oncol.* 19:330-338 (1993).

Kilmer et. al., "The Q-switched Nd:YAG laser effectively treats tattoos, " *Arch. Dermatol.* 129:971-978 (1993).

Leonard, "Starch granulomas," *Arch. Dermatol.*, 107:101-103 (1973).

Levins et al., "Q-switched ruby laser treatment of tattoos," *American Society for Laser Medicine and Surgery Abstracts*, 63, Abstract No. 255 (1991).

Loewenthal, "Reactions in green tattoos," *Arch. Dermatol.*, 82:129-135 (1960).

Mann et al., "Electron-microscopic investigation of tattoos in rabbit skin," *Arch. Dermatol. Res,.* 271:367-372 (1981).

Novy, "A generalized mercurial (cinnabar) reaction following tattooing," *American Medical Assn.* 49:172-173 (1944).

Ort et al., "$CO_2$ laser resurfacing of tattoos prior to Q-switched laser treatment," *American Society for Laser Medicine and Surgery Abstracts*, 26 (suppl. 12):23, Abstract No. 91 (2000).

Rajca et al., "Magnetic ordering in an organic polymer," *Science*, 294:1503-1505 (2001).

Reid et al., "Tattoo removal by $CO_2$ laser dermabrasion," *Plast Reconstr Surg.*, 65(6):717-728 (1980).

Reid et al., "Q-switched ruby laser treatment of black tattoos," *Br. J. Plast. Surg.*, 36:455-459 (1983).

Scutt, "The chemical removal of tattoos," *Br. J. Plast. Surg.*, 25:189-194 (1972).

Taylor et al., "Light and electron microscopic analysis of tattoos treated by Q-switched ruby laser," *J. Invest. Dermatol.*, 97:131-136 (1991).

Weissleder et. al., "Superparamagnetic iron oxide: pharmacokinetics and toxicity," *American Journal of Roentgenology*, 152(1):167-173 (1989).

\* cited by examiner

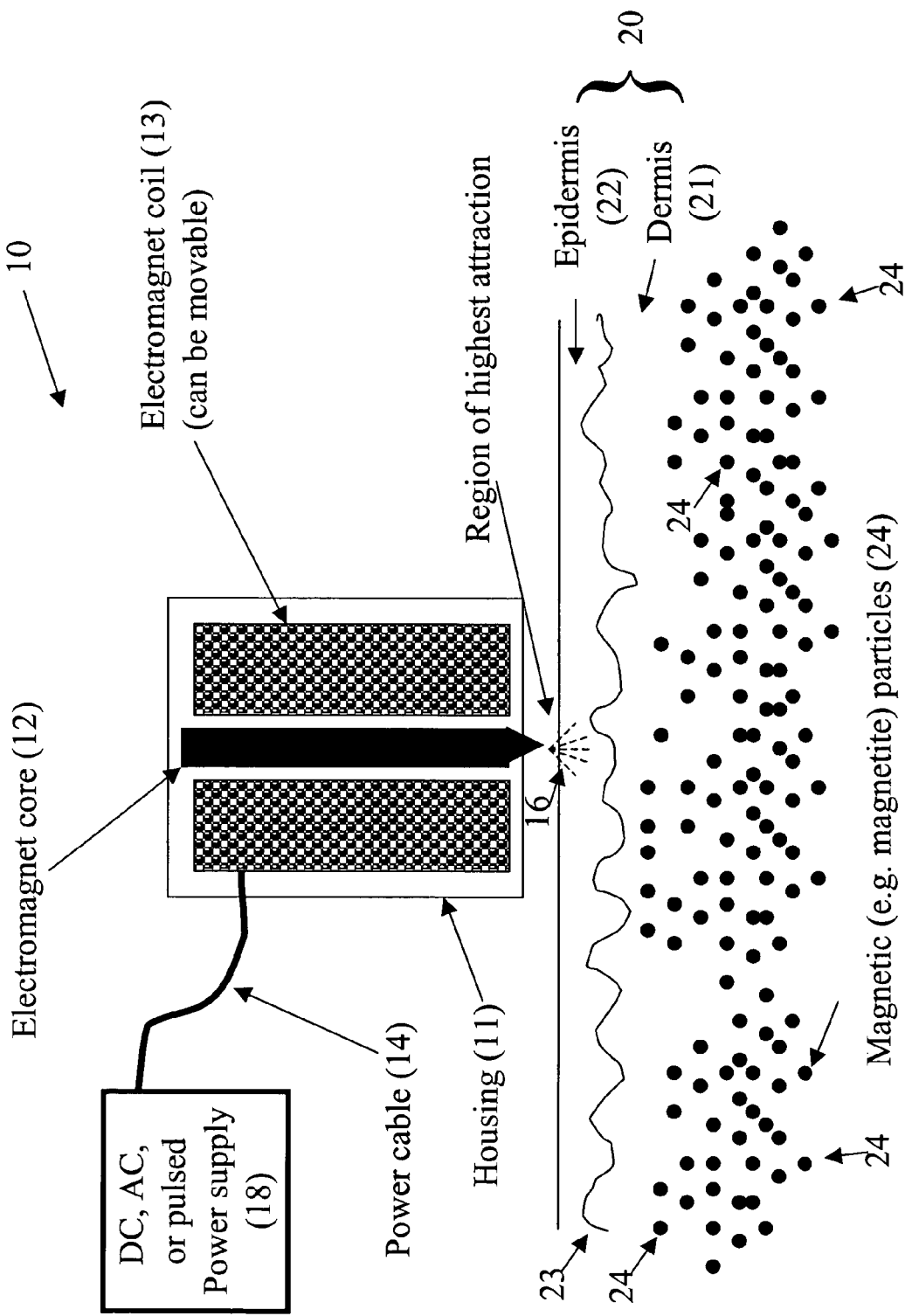

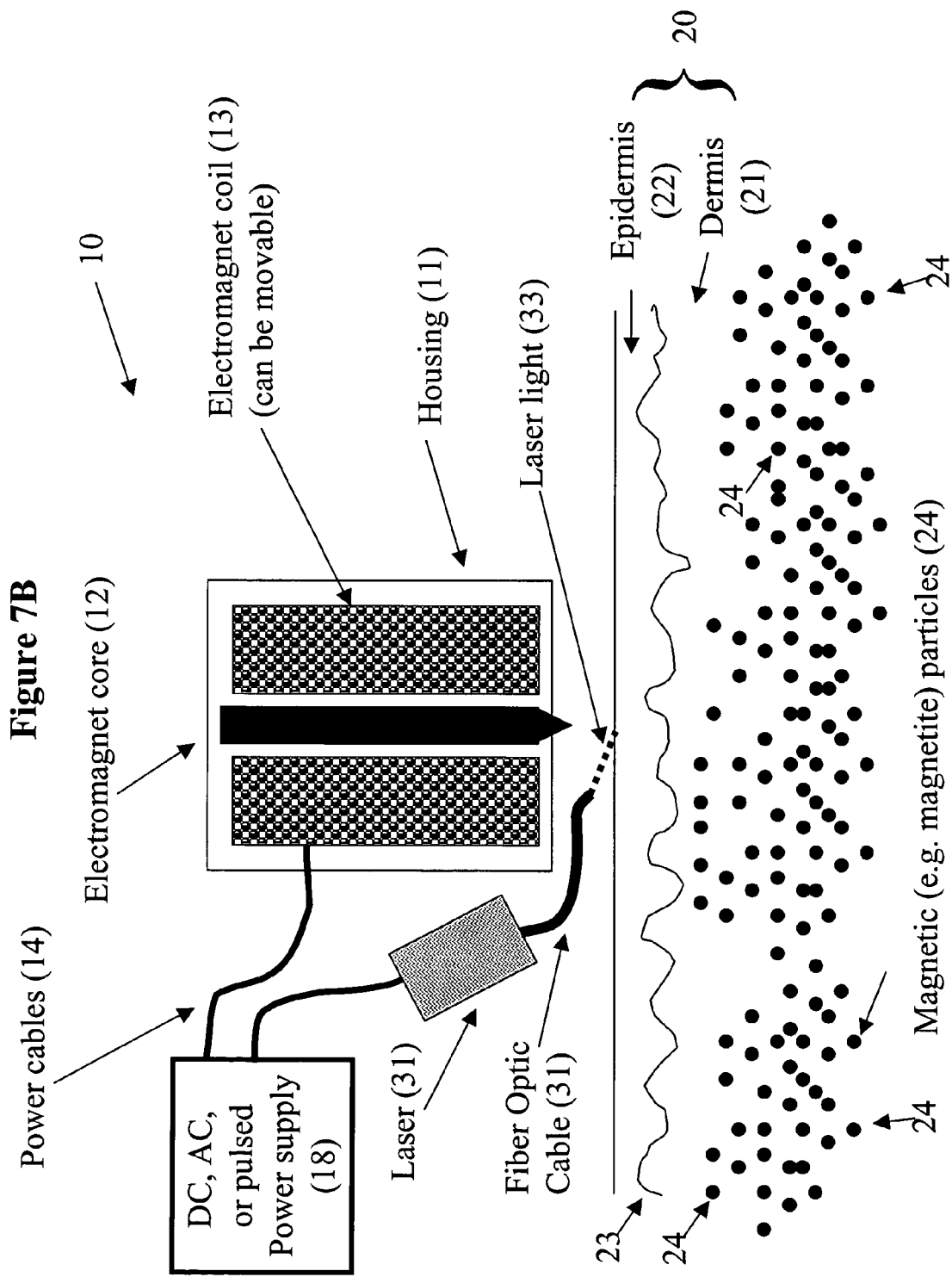

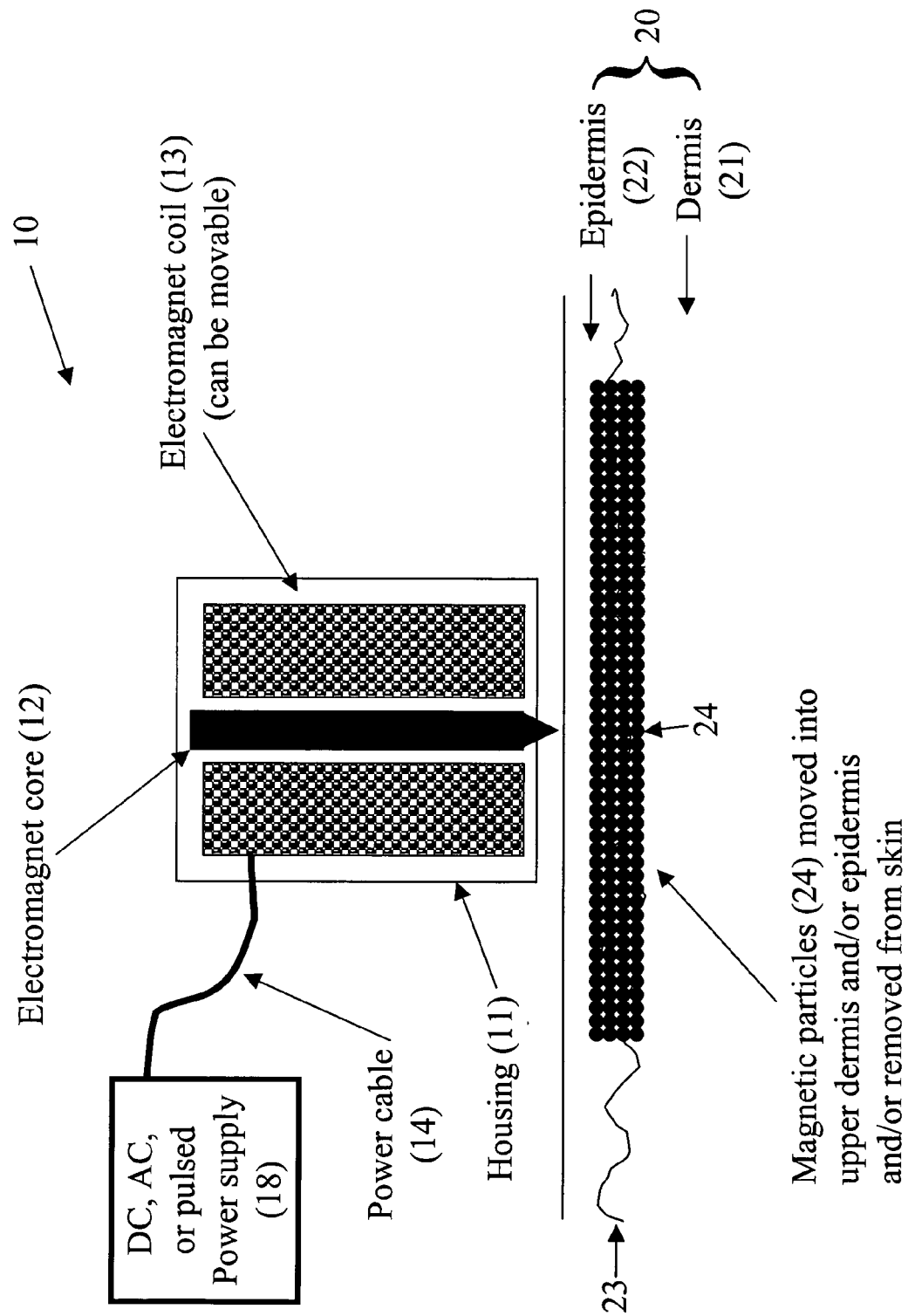

MAGNETIC INK TISSUE MARKINGS

CLAIM OF PRIORITY

This application claims priority under 35 USC §119(e) to U.S. Provisional Patent Application Ser. No. 60/493,230, filed on Aug. 6, 2003, the entire contents of which are incorporated by reference herein.

TECHNICAL FIELD

This invention relates to tissue markings, e.g., tattoos, and more particularly to magnetic particle tissue markings.

BACKGROUND

Tattooing is an ancient art, dating back as early as 12,000 BC (Grumet, *Am. J. Orthopsychiatry,* 53:482-492 (1983)), when ash was rubbed into skin incisions. Puncture tattooing later became popular and is practiced even today. Modern tattoo inks cover a wide pallet of colors and use different tattoo "inks." Today, about 1 in 5 young adults in the United States have been injected with these substances, by people with little or no medical training.

The desire to remove tattoos is probably as old as their existence. The fraction of tattooed people who will seek tattoo removal is unknown, but substantial. The earliest report of tattoo removal was by Aetius, a Greek physician who described salabrasion in 543 AD (Scutt, *Br. J. Plast. Surg.,* 25(2):189-194 (1972)). Grossly destructive methods such as dermabrasion and argon or $CO_2$ laser vaporization are still used (Apfelberg et al., *Br. J. Plast. Surg.,* 32:141-144 (1979); Apfelberg et al., *Ann. Plast. Surg.,* 14:6-15 (1985); Bailin et al., *J. Derm. Surg. Oncol.,* 6(12):997-1001 (1980); Reid and Muller, *Plast. Recons. Surg.,* 65(6):717-728 (1980)), but they have a high risk of scarring. Leon Goldman first reported laser tattoo removal in 1965 and then in 1967 using a Q-switched ruby laser (Goldman et al., *J. Invest. Dermatol.,* 44:69-71 (1965)); Goldman et al., *JAMA,* 201 (11):841-844 (1967)). Later cases reported by Reid et al. (*Br. J. Plast. Surg.,* 36:455-459 (1983)) revealed good results with a Q-switched ruby laser, particularly when used on black and amateur tattoos. These results were further refined based on concepts of selective photothermolysis (Anderson and Parish, *Science,* 220:524-527 (1983)).

Because of the variety of tattoo ink colors, a variety of laser wavelengths are necessary to remove colored tattoos. High-energy Q-switched ruby (694 nm), alexandrite (755 nm), Nd:YAG (1064 nm) and frequency-doubled Nd:YAG (532 nm), lasers are now used, which emit visible and near-infrared light pulses ranging from about 10-100 ns duration (Levins et al., *Lasers Surg. Med. Suppl.,* 3:63 (1991); Kilmer and Anderson, *Dermatol. Surg. Oncol.,* 19:330-338 (1993); Kilmer et al., *Arch. Dermatol.,* 129:971-978 (1993); Fitzpatrick and Goldman, *Arch. Dermatol.,* 130(12):1508-1514 (1994)).

Before laser treatment, tattoo ink particles are typically found within dermal fibroblasts and mast cells, predominantly in a perivascular location (Mann and Klingmuller, *Arch. Dermatol. Res.,* 271:367-372 (1981)). The mechanism by which Q-switched lasers remove tattoos involves selective rupture of these cells, breakdown of tattoo ink particles, and ink removal by transepidermal elimination and/or lymphatic transport (Taylor et al., *J. Invest. Dermatol.,* 97:131-136 (1991); Ferguson et al., *Br. J. Dermatol.,* 137:405-410 (1997)). The risk of scarring after Q-switched laser treatment is substantially lower than after excision, dermabrasion, or $CO_2$ laser vaporization. However, much of the ink remains inside the body, either in regional lymph nodes or as a lightened, residual tattoo in the skin. The number of Q-switched laser treatments required for complete tattoo "removal" depends on the type of tattoo ink, body location, and laser. Amateur tattoos made with carbon (ash, graphite, India ink) respond best, typically clearing in most patients after 4-6 treatments. Multicolored tattoos on the extremities tend to respond poorly. Typically, less than half of these tattoos can be cleared in less than ten treatments, regardless of the type of Q-switched lasers used.

Tattoo inks are probably the least-regulated substances routinely injected into people in our society. The purity, pharmacology, biodistribution, and identity of most inks are unknown. None are approved by the Food and Drug Administration (Anderson, *N. Engl. J. Med.,* 326:207 (1992)). New bright-colored inks are being introduced at an unknown rate, and are often those most difficult to remove by laser treatment. Although most tattoos appear to be well tolerated, there are reports of infection, photosensitivity, and acute and chronic hypersensitivity reactions (Novy, *Arch. Dermatol.,* 49:172-173 (1944); Bjornberg, *Arch. Dermatol.,* 88:83-87 (1963); Loewenthal, *Arch. Dermatol.,* 107:101-103 (1973); Goldstein, *J. Dermatol. Surg. Oncol.,* 5:896-900 (1979)). Tattoo ink is permanently taken up in lymph nodes in addition to the intended target organ, skin. The long-term health risk of tattooing is unknown. The present situation may eventually lead to significant problems.

In view of the history, popularity, limited safety data and limited treatment options for tattoos, safe, removable tattoo inks are desirable.

SUMMARY

The present invention is based, in part, on the discovery that magnetite ($Fe_3O_4$) particles can be grossly and microscopically moved through living skin by external magnetic fields, and thus can be used to make safe, removable tissue markings, e.g., tattoos. Thus, the invention provides novel "magnetic tattoo inks" comprising magnetic particles, e.g., magnetite particles, methods for making tissue markings using the inks, and methods and devices for removing tattoos made using conventional black magnetite inks and/or the new magnetic inks described herein. The magnetic particles can be of any size suitable for use in tissue markings, but are typically in the micrometer or sub-micrometer range, e.g., a range from about 0.1 to 5 micrometers, e.g., about 1 to 5 micrometers, and should be uniform in size, e.g., vary by about, or less than, a factor of two, e.g., less than about 1 micrometer.

The magnetic particles can be black (e.g., the natural color of pure magnetite), or otherwise colored, e.g., coated or compounded with a chromophore. In some embodiments, the particles can be coated, e.g., with a clear or colored coating, e.g., a biocompatible, indispersible, and/or biologically inert coating to change the color of the particles, protect the particles, and/or render them more inert. In some embodiments, the coating can be or can include a chromophore, metal oxide, silica, glass, fluorocarbon resin, organic or inorganic polymer, wax, or any combination thereof. In some embodiments, the ink includes magnetic particles of one color and non-magnetic particles of another color, e.g., the magnetic particles are blue and the non-magnetic particles are yellow, or vice-versa. The colors blue and yellow are used for illustrative purposes only, and any colors can be used. In some embodiments, the mixture of particles of two colors produces magnetic ink of a third color; using the example of blue and yellow, the ink could appear green.

In one aspect, the invention provides a sterile magnetic ink composition including magnetic particles, e.g., magnetite ($Fe_3O_4$) particles, wherein the magnetic particles are from 1.0 to 5 mm in diameter, and vary in diameter by less than a factor of about two. In some embodiments, the ink also includes a carrier, e.g., ethanol; purified water; witch hazel; Listerine™ antiseptic mouthwash propylene glycol; glycerol; denatured alcohols; methanol; isopropyl alcohol; ethylene glycol; formaldehyde; glutaraldehyde; surfactants; and detergents.

In another aspect, the invention features a method of making a magnetic ink tissue marking, by implanting a magnetic ink composition described herein into the tissue, e.g., skin. For example, the method can include implanting the magnetic tattoo ink composition to form a pattern in the tissue, such as a name, e.g., the name of a loved one, or a celebrity, or a sports team. In some embodiments, the method also includes implanting a non-magnetic tattoo ink composition to form another pattern, to form a design that includes both the magnetic and non-magnetic ink patterns. The magnetic tattoo ink composition and non-magnetic tattoo ink composition can be the same or different colors; in some embodiments, the pattern formed by the implanted magnetic tattoo ink composition is a name, and the pattern formed by the implanted non-magnetic tattoo ink composition is a background for the name. These patterns enable the removal of the named without disturbing the background.

In another aspect, the invention features a method of altering the appearance of a magnetic ink tissue marking including magnet-attracting particles as described herein by applying a magnetic field to the tissue sufficient to move the particles to alter the appearance of the tissue marking. In some embodiments, the method includes applying a laser treatment, e.g., a Q-switched ruby laser treatment, before applying the magnetic field. In some embodiments, all or a part of the epidermis is removed locally, or the dermo-epidermal junction is disrupted before the magnetic field is applied. In some embodiments, the magnetic field is applied to the tissue for a length of time sufficient to cause the magnetic ink tissue marking to appear darker or to lighten or remove the magnetic ink from the tissue. In some embodiments, either the application of a magnetic field, the application of a Q-switched ruby laser treatment, or both, is repeated until the magnetic ink has been altered, e.g., darkened, lightened, or removed from the tissue. Thus, the method can be used to remove a particular color or pattern that comprises magnetic ink from the skin, e.g., removing a name; if the same location was tattooed with non-magnetic ink, the method can be modified so that patterns formed by the non-magnetic ink remain in the skin, e.g., by modifying the intensity or wavelength of the laser treatments.

In another aspect, the invention features a device for removing magnetic ink skin tattoos, the device including means for producing a high product of the magnetic field strength and magnetic field gradient within the skin, e.g., at least one magnet, e.g., a permanent magnet or an electromagnet, e.g., a superconducting electromagnet or a solenoid coil and a housing configured to enable the device to be contacted to the skin in the location of a tattoo. In some embodiments, the device includes a controller that can be used to vary the magnetic field spatially or temporally, or both. In some embodiments, the device includes a laser, e.g., a Q-switched ruby laser, such as a laser used in a conventional laser treatment device.

In a further aspect, the invention provides methods for attaching magnetic objects to a portion of skin, by implanting a magnetic tattoo ink composition as described herein in a manner sufficient to create a magnetic area on the skin, and attaching a magnetic object to the skin. In some embodiments, the magnetic tattoo ink composition is substantially the same color as the skin, and so is invisible to the naked eye.

As used herein, an "indispersible" substance (such as a coating material or an individual particle) does not disintegrate, dissolve, or become metabolized in tissue. An "inert" or "biologically inert" substance or material (such as the coating material of a particle) generally creates no significant biochemical, allergic, or immune response after the normal healing period when implanted into living tissue.

The invention provides several advantages. For example, magnetic ink tissue markings can be altered, e.g., changed, updated, or removed, by the application of a magnetic field, or by the application of a treatment to free the particles from engulfing cells, e.g., laser treatment, followed by application of a magnetic field.

Magnetite ($Fe_3O_4$) is a non-toxic, insoluble, stable, jet-black compound, which can be used to make tissue markings that can be altered by both lasers and external magnetic fields. Thus, an individual can now choose to have a tattoo that can be more easily removed or altered than tattoos made using conventional tattoo inks and removed using conventional techniques. The removal methods of the invention are applicable to, e.g., can be used to remove, both the magnetic inks described herein, and to tattoos made with conventional inks that have magnetic particles.

As used herein, "magnetic" means capable of being attracted by a magnet, or capable of being magnetized. As used herein, a "magnetic particle" refers to a particle that is a magnet, or is capable of being attracted by a magnet, e.g., capable of being magnetized, e.g., a particle comprising in whole or in part $Fe_3O_4$.

As used herein, a "permanent tissue marking" or "tissue marking" is any mark created by the introduction of particles into tissue, typically living tissue, with the intention of permanent or long-term endurance. Markings can be any color and can be detectable, for example, by the naked eye, when exposed to electromagnetic radiation in one or more regions of the spectrum, for example, the visible or near-infrared regions. A permanent marking is generally a marking that remains visible or otherwise detectable (e.g., under the proper illumination) until it is exposed to a specific energy.

As used herein, a "tattoo" is a type of tissue marking wherein the tissue is usually skin. "Standard tattoos" and the inks and pigments used to create them do not typically have strong magnetic properties.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples included herein are illustrative only and not intended to be limiting; methods and materials similar or equivalent to those described herein can also be used in the practice of testing of the methods and compositions described herein.

Other features and advantages of the invention will be apparent from the following detailed description, and from the claims.

DESCRIPTION OF DRAWINGS

FIGS. 7A, 7B, and 8 are line drawings showing cut-away, not to scale views of a simple hand-held electromagnet device, before application of a magnetic field (FIG. 7A) and after (FIG. 8); FIG. 7B shows the inclusion of a laser.

DETAILED DESCRIPTION

Figure 1A:
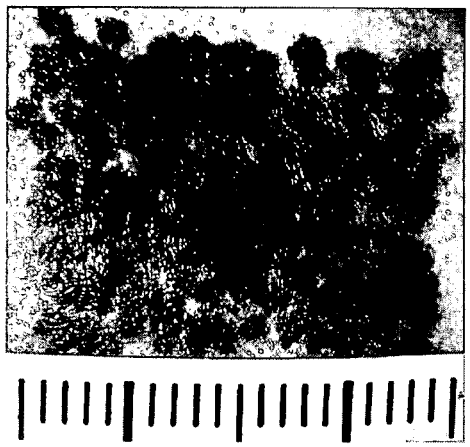
FIGS. 1A-1D are photographs showing the appearance of magnetite tattoos on an albino rat. 1A, untreated mature tattoo. 1B, immediately after Q-switched ruby laser (QSRL) treatment, showing immediate whitening. 1C, magnet affixed to a magnetite tattoo, held in place by magnetic attraction. 1D, magnet sutured in place after laser treatment, for 3-week application.

It has been demonstrated that tissue markings (e.g., tattoos) comprising micrometer-sized magnetic particles (e.g., magnetite) can be grossly and microscopically manipulated in vivo by external magnetic fields. Magnetic particles, e.g., magnetite particles, can be successfully used to create tissue markings, e.g., tattoos, which can be altered, e.g., changed, updated, or removed, by the application of magnetic fields.

Magnetite is a biodegradable, biocompatible, non-toxic molecule that has been used as an MRI contrast agent (Weissleder et al., *Am. J. Roentgenol.*, 152:167-173 (1989)). Other magnetic particles, such as red and black iron oxides ($Fe_2O_3$, FeO, and $Fe_3O_4$) can also be used in the new methods. Unlike other tattoo inks, iron oxides have not been reported to cause hypersensitivity reactions. The most common tattoo ink color is black, and, as demonstrated herein, magnetite makes black tattoos nicely. A pure, sterile, optimized suspension of magnetite can be produced as an alternative to other black inks, which can include carbon and FeO. Magnetic inks can also be produced in colors other than black, for example by coating magnetic particles, e.g., magnetite particles, with a chromophoric substance.

Magnetic Ink for Tissue Markings

In some embodiments, the invention includes a composition suitable for use in tissue marking, e.g., a "magnetic ink," including magnetic particles, e.g., magnetite particles. The particles can be of any size suitable for use in tissue markings, but are typically in the micrometer or sub-micrometer range, e.g., about 0.1 to 5.0 micrometers, e.g., about 1 to 5 micrometers. Typically, the particles will comprise magnetite ($Fe_3O_4$), but a number of components can equally be used, e.g., metals (including the magnetic elements, such as iron, nickel, cobalt, chromium, or manganese) or magnetic organic polymers (see, e.g., Rajca et al., *Science*, 294:1503-1505 (2001)). The particles can be made of 100% metal oxide (e.g., magnetite), or can be composites including other components, e.g., polymers, e.g., polymer-bonded magnets, and/or polymers comprising chromophores. In some embodiments, the ink comprises polymer particles filled with magnetic, e.g., magnetite, nanoparticles. In some embodiments, the particles are encapsulated with an inert, colored coating, e.g., a polymer comprising a chromophore to form microspheres.

Unlike conventional magnetite-containing black tattoo inks currently in use, which comprise magnetite particles that can vary dramatically in size (e.g., by about an order of magnitude), typically, the magnetic particles described herein will be of a uniform size, e.g., vary in diameter by less than a factor of two, e.g., 1-2 micrometers. In some embodiments, the particles are, for example, about 1-2 micrometers, about 2-4 micrometers. In some embodiments, the diameter of the particles varies by less than about 1 micrometer, e.g., about 0.75 micrometers, about 0.5 micrometers, about 0.25 micrometers, or about 0.1 micrometers.

In some embodiments, the particles are magnetized, e.g., capable of attracting iron (e.g., project their own magnetic field), and producing a magnetic field outside themselves, either naturally or by induction. In some embodiments, a magnetic field can be induced in the particles, e.g., during manufacture and/or after implantation into the tissue, by exposing the particles to a strong magnetic field, e.g., an electromagnet. In some embodiments, the magnetic field created is from about 200 to about 25,000 or more gauss, e.g., 500, 800, 1000, 2500, or 12,500 gauss (10,000 gauss=1 Tesla). In some embodiments, the magnetic particles retain the ability to project a magnetic field, i.e., they become permanent magnets. In some embodiments, the particles may lose the ability to produce a magnetic field over time, and a field can be re-induced by re-application of a strong magnetic field.

The magnetic particles can be fabricated using methods known in the art, including, but not limited to, mechanical milling, supercritical $CO_2$-based precipitation of magnetite/polymer microparticles, or micelle synthesis. After fabrication, the particles can be sorted for size and quality, e.g., by centrifugation or filtration. A number of magnetic particles are commercially available, e.g., from Ademtech, 33600 Pessac, France; Bangs Laboratories Inc., Fishers, Ind., U.S.A.; Pea Ridge Iron Ore Co., Sullivan, Mo.; Quantum Magnetics, Division of Clemente Associates Inc., Madison, Conn., U.S.A.; and many others. A list of manufacturers can be found on the world wide web at magneticmicrosphere- .com/supply.htm. The particles can be sterilized using methods known in the art, e.g., heat, chemical, or radiation sterilization.

The magnetic particles can be black or colored, e.g., coated with or synthesized with a chromophore, e.g., any chromophore typically used in tissue marking applications, e.g., colored or white tattoo ink, or, for example, any colored substance approved by the United States Food and Drug Administration for use in humans, e.g., rifampin, β-carotene, tetracycline, indocyanine green, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), or FD&C Yellow No. 6 (Sunset Yellow FCF).

In some embodiments, the magnetic particles can be coated, e.g., with a clear coating, e.g., a substantially visibly transparent, biocompatible, indispersible, and/or biologically inert coating to protect the particles or render them more inert. Substances fitting these criteria that are capable of encapsulating particles useful in the new compositions include waxes with a melting point substantially above body temperature, for example, natural waxes, synthetic waxes, and wax mixtures, specifically Polywax® and carnauba wax; plastics and organic polymers, for example, parylenes, polyamide, polyvinyl acetate, urea formaldehyde, melamine formaldehyde, ethylene acrylate, cyanoacrylates, butadiene-styrene, and specifically biocompatible materials such as Epo-Tek® 301 and/or 301-2, manufactured by Epoxy Technology, Billerica, Mass.; metal oxides, for example, $TiO_2$, silica ($SiO_2$), BIOGLASS®, KG-3 and BG-7 manufactured by Schott, Inc., Germany, and other glasses ($SiO_2$ plus any one or more of the following: $Na_2O$, CuO, $B_2O_3$, MgO, $Al_2O_3$, $P_2O_5$, and others); inorganic fluorine-containing compounds such as $MgF_2$; and fluorocarbons such as TEFLON®. In some embodiments, the coating is a noble metal, e.g., Ag, Au, or Pt. The material for coating should not interfere with the magnetic properties of the particle.

In some embodiments, the magnetic particles are coated first with a chromophore, and then with a clear outer coating.

In some embodiments, the particles are provided dry, e.g., substantially free of any liquid carrier. In some embodiments, the particles are provided in a concentrated liquid form, e.g., to be diluted before use or application, or in a concentration suitable for use directly. In some embodiments, the particles can be provided in, or diluted into, a carrier, e.g., a carrier known in the art, including but not limited to ethyl alcohol (ethanol); purified water; witch hazel; Listerine™ antiseptic mouthwash; propylene glycol; glycerin (glycerol); denatured alcohols; other alcohols (methyl alcohol or methanol and isopropyl alcohol or rubbing alcohol are commonly used); ethylene glycol; aldehydes, such as formaldehyde and glutaraldehyde; or various surfactants or detergents. The carrier can be clear, e.g., not imparting any color to the skin, or colored. In some embodiments, the particles are mixed into a standard, non-magnetic tattoo ink, to provide a colored and magnetic tattoo. A number of standard tattoo inks are known in the art and are commercially available. In some embodiments, powdered standard ink can be dissolved into the magnetic ink of the invention. In other embodiments, powdered standard ink and dry particles of the invention are dissolved together in a suitable carrier. In some embodiments, the magnetic inks of the invention will be provided in one or more colors, e.g., colors in addition to or instead of black, and a manegtic, colored tissue marking can be created using only manegtic inks. In some embodiments, the manegtic ink comprises magnetic particles of one color and non-manegtic particles of another color. When such an ink is used to make a tissue marking, the marking has a color resulting from the mixture of the two (e.g., blue manegtic particles plus yellow non-manegtic particles make green ink). At a later date, the manegtic particles can be removed, e.g., by a methods described herein, leaving only the non-manegtic particles, thus changing the color of the tissue marking.

Methods of Making Tissue Markings

The magnetic inks can be used to make any type of tissue marking, including artistic tattoos ("body art"), or for identification. Some examples of markings to fill identification needs include markings to assist tracking bodily sites of medical interest in external and superficial internal tissue, for example, marking a radiation therapy field on the skin, or marking a colon polyp in the intestine which can subsequently be monitored endoscopically; identification markings for humans, for example, emergency information regarding an individual's medical history, "dog-tags" on military personnel, and identification markings on newborn babies to ensure no hospital mix-ups; and identification markings for animals (such as wild animals, livestock, sport/show animals, and pets), for example, information markings for the return of lost pets.

The magnetic inks of the present application can be applied using conventional tattooing methods and equipment, e.g., standard oscillating spring point machines such as the commercially available Technical, Paolini, Joe Kaplan, Black Lotus, or Mao Tattoo Machine. The magnetic inks can be applied using standard or specialized tattoo needles, such as are described in U.S. Pat. No. 6,345,553. The magnetic inks can be applied alone or with other inks, e.g., standard colored tattoo inks, e.g., mixed together or applied separately.

The compositions can be tested by injection into the dermis of an animal, e.g., a guinea pig, a Yucatan micropig, a fuzzy rat, or a hairless albino rat, at different amounts of delivered material, e.g., with a standard oscillating tattooing machine. Healing of the skin can be allowed, e.g., for about one month, and the quality and darkness of the tattoos can be observed and measured, e.g., using a collimated light source and digital camera apparatus. Skin reactions to the tattoo can also be observed, e.g., for signs of persistent inflammation, elimination and stability of the tattoos, e.g., over an extended period of time, e.g., weeks, months, or more. The amount of material needed for providing a given line or darkness can also be measured.

The magnetic ink compositions described herein can be used to make tissue markings that can be altered, e.g., removed, by the application of a magnetic field, e.g., an external magnetic field. The tissue markings can include markings made using conventional inks and/or inks including both magnetic and non-magnetic particles, thus, the application of the magnetic removal methods of the present invention will alter the magnetic portion, but can leave the non-magnetic portion untouched. As one example, non-magnetic inks can be used to make a background design, and magnetic inks can be used to inscribe the name of a person, e.g., a significant other. If the relationship later ends, the person's name can be removed, leaving the background design.

Tattoo Alteration Methods

The invention also includes methods for the alteration, e.g., removal, of tissue markings comprising, e.g., the magnetic inks described herein, or conventional black ink comprising magnetite particles.

In some embodiments, magnetic fields alone can be used to alter or extract magnetic ink tattoos, i.e., without the need for laser treatment to free particles from within dermal cells. As described in the Examples below, 1.4 µm magnetite particles, implanted as a tattoo in rat skin, can be manipulated using external magnetic fields (see also, Huzaira and Anderson, *Lasers Surg Med.*, 31:121-128 (2002)). Although application of magnets for an hour to mature magnetite skin tattoos in rats, without laser treatment, did not cause significant ink particle movement by histological analysis (p=0.133), there was re-arrangement of the magnetite, as evidenced by streaking along magnetic field lines (see Example 1 and FIG. 3A). Tattoo ink is typically contained in cells, mainly macrophages, fibroblasts, and mast cells. Although the magnetic forces produced for 1 hour under the conditions described in Example 1 (below) were apparently not sufficient to overcome cell-matrix adhesion in the dermis, long-term application of magnets to tattoos, and/or more powerful magnetic fields, can "drag" cells, loaded with magnetic particles, through the dermis, thus removing the tattoo. The force exerted on a magnetite particle within the dermis by a magnetic field is proportional to the product of the magnetic field strength and the magnetic field gradient.

In some embodiments, a treatment is applied in combination with magnetic field use, e.g., before application of a magnetic field for extraction of magnetite particles, which "frees" the particles from cells in the dermis, e.g., a treatment that can be used to selectively destroy the cells enclosing the particles, e.g., a laser treatment, such as a Q-switched laser treatment, which heats the particles sufficiently to "boil" water molecules surrounding the particles, thus rupturing the cells in which the particles are imprisoned. Alternatively or in addition, one or more powerful pulses from an electromagnet can be used to "free" the particles, and the same or another magnetic device can then be used to attract the particles for removal from the skin, after which the ink particles can be more easily dragged through the dermis toward a magnet at the skin surface. In the dermis, the particles line up along what appear to be magnetic field lines. Some particles can be physically extracted within an hour, if the epidermis is not intact. As one theory, not meant to be binding, the magnetite particles traverse the dermis until they reach an intact dermo-epidermal junction, which acts as a barrier. Magnets applied for several weeks after laser treatment cause a darker tattoo, probably by bringing more of the ink into the upper dermis. Thus, laser treatment followed by selective long-term application of magnets, or long-term application of magnets alone, can be used to darken or remove selected areas or all of a tattoo. In some embodiments, the method includes repeating the laser treatment and/or application of magnetic field until the magnetic ink has reached a desired lightness (e.g., been removed), or darkness (e.g., a desired amount of the magnetic ink has been brought to the surface of the tissue).

The fact that micrometer-sized particles can be easily forced to traverse the dermis is remarkable and unexpected. The broad implication for tattoo removal is that a Q-switched laser treatment followed by any adjunctive treatment which enhances and/or forces particle motion, provides an effective method to remove tattoos. While magnetic fields are a convenient and effective model system, this is not the only means for forcing particle motion. For example, more mechanical means, such as tissue massage using gross vibratory motion or alternatively ultrasonic vibratory motion applied after laser treatment and/or a directed flow of extracellular fluid to wash particles through the dermis, can be employed.

The present results indicate that the epidermis or dermo-epidermal junction may block extraction of tattoo ink. Therefore, intentional removal of the epidermis followed by forced-ink-extraction, e.g., using a magnet, will also be effective. For example, the dermo-epidermal junction can be disrupted using a $CO_2$ laser (Ort et al. (*Lasers Surg. Med.*, 26 (suppl 12):23 (2000)).

An alternative to ink extraction would be to force ink in the opposite direction—to the bottom of the dermis and "out of sight." As demonstrated herein, long-term application of a magnet to intact skin after laser treatment darkened the tattoo by moving ink into the upper dermis. By placing the magnet under the skin, e.g., surgically implanted, the magnet would attract the magnetic ink deeper into the tissue and the tattoo would lighten. Alternatively, the particles can be provided with a specific charge, and a device to drive the particles deeper into the skin would have an opposite charge.

Vertical streaking of magnetic tattoos in the dermis was uniquely associated with magnet application. The streaking pattern is consistent with magnetic field lines, which can be seen in any setting where paramagnetic or superparamagnetic particles are free to move in response to a permanent magnet. The particles clump together and form an oriented streak because of particle-particle interactions. Within each particle, magnetic polarization occurs in response to the external magnetic field, such that each particle becomes a small magnet. Head-to-tail alignment of particles along the external magnetic field then occurs. Thus, a stationary magnetic field can be used to create lines in the tissue marking along the field.

Alternatively, a time-varying magnetic field can be used, e.g., to bring the magnetic particles to the surface in a more uniform manner, or to extract the magnetic particles from the dermis. Alignment and clumping of magnetite tattoo particles within the skin of rats occurs along the field lines of a permanent magnet applied to a magnetite skin tattoo, as described. This alignment is due to interactions between adjacent particles' magnetic fields, and the clumping tends to limit extraction of individual particles. An advantage of a time-varying magnetic field, e.g., a field which is modulated such that its polarity switches, is that particle clumps will tend to dissipate more, as compared with the particle clumps in a static magnetic field. As one theory, not meant to be binding, some particles may enter cul-de-sacs created by extracellular matrix proteins and various skin structures.

A spatially-varying magnetic field would minimize this problem. A spatially-varying magnetic field is a field in which the spatial contours, locations, and/or shape of the magnetic field lines change over time. This can be accomplished by physically moving a permanent magnet or magnets over the skin containing a magnetite tattoo, to spatially vary the magnetic field within the skin tissue. Spatial variation can also be achieved by activation of different coils within a multi-coil electromagnet, which may or may not be physically moved over the skin tissue. Thus, a time- and spatially-varying magnetic field can be used, e.g., to more completely extract the magnetic particles.

Magnetic tattoo manipulation can be optimized, e.g., by varying the choice of magnets, magnetic field strength, magnetic field gradient, time of application, magnetic particle size and strength, and other factors. For example, permanent magnets having a field force of at least about 0.5 Tesla, e.g., about 1 Tesla, about 1.5 Tesla, about 2 Tesla, or more, can be used. The magnets can be applied for varying periods of time, e.g., 1 hour, 1 day, 1 week, several weeks, a month, or several months. The motive force exerted by a magnetic field on a paramagnetic material (such as $Fe_3O_4$) is approximately proportional to the magnetic moment of the particle, and to the product of the magnetic field strength and the local magnetic field gradient. Although there are intrinsic limitations to the field strength and gradient of permanent magnets, electromagnets can be constructed specifically for tattoo manipulation, thus offering the options of higher field strength, pulsing and/or switching of the field polarity. Such electromagnets are known in the art and can be constructed by one of ordinary skill in the art, or can be purchased from a commercial or custom supplier. For example, solenoid coils are commercially available electromagnets that span a range of sizes and strengths. For much more powerful fields, superconducting (cold) electromagnets can also be used. These are most commonly used in medicine for magnetic resonance imaging (MRI), which must produce a stable magnetic field across the entire human body. Much smaller superconducting electromagnets producing field strengths up to approximately 20 Tesla could be used for magnetic tattoo extraction.

Devices for Altering Magnetic Tattoos

As noted above, the force exerted on a magnetic particle within the dermis by a magnetic field is proportional to the product of the magnetic field strength and the magnetic field gradient. Thus, the invention also includes devices, useful in practicing the methods described herein, which are capable of creating a high product of the magnetic field strength and the magnetic field gradient. Suitable devices can be used to create an external magnetic field that can be used to alter, e.g., remove magnetic ink tissue markings, e.g., magnetite tattoos. Such devices can comprise external permanent magnets or electromagnets suitable for use in the methods described herein. Such devices can include controlling devices capable of producing a time-varying, spatially-varying, and/or time- and spatially-varying magnetic fields.

FIGS. 7A and B are schematic diagrams showing a cut-away, not to scale view of one embodiment of the new devices, comprising a simple hand-held electromagnet device 10, arranged within housing 11, configured specifically to produce a high product of the field×field gradient near a pointed or tapered soft-iron core 12, which is placed in or near contact with the skin 20. DC or alternating or pulsed current is generated by a power supply 18, and transmitted via flexible cable 14 to electromagnetic coil 13 to produce the magnetic field 16. The power supply 18 can be internal to the housing, e.g., a battery, or external, e.g., the device can be plugged into an outlet. If alternating or pulsed current is supplied, the magnetic field will be time-variant. The device 10 is intended to be held in or near contact with skin, and passed along the skin surface to produce a spatially-varying magnetic field. Other details of the device are known in the art, e.g., supporting structures, user interface, power supply controls, etc., all of which are well known in the art of making electrically-powered medical devices. The desired peak magnetic field strengths range up to about 20 Tesla, and are more typically around 0.5-5 Tesla, at the "business" tip of the device.

During treatment, magnetic particles 24 in the dermis 21 are attracted to and migrate toward the device's tip, entering the upper dermis, epidermis 22, and/or extracted from the skin 20. In FIG. 8, the particles 24 have migrated to the upper dermis 21 and epidermis 22. The dermo-epidermal junction 23 is at least a partial barrier for migration of particles 24 into epidermis 22. Once in the epidermis 22, the particles 24 will be naturally shed over the period of about one month, because the epidermis 22 is constantly growing outward and shedding.

In some embodiments, it may therefore be desirable to remove the epidermis, or the epidermis and the upper dermis, either before or after application of the magnet, e.g., using dermabrasion or laser resurfacing. These procedures for removing epidermis and upper dermis do not cause permanent scars when properly performed to a depth of about 0.1-0.3 mm (this limits the depth to the epidermis and upper, so-called papillary, dermis). Alternatively, suction can be applied to the skin to create a suction blister at the dermo-epidermal junction (a separation between the dermis and epidermis, which can be induced by methods known in the art, e.g., devices such as those described in Kiistala, *J. Invest. Dermatol.*, 50(2): 129-37 (1968), with or without the application of heat), either before or after the application of a magnetic field as described herein. Once the particles are brought to the junction, the particles will end up in the blister fluid filling the suction blister, and can be quickly removed, e.g., by removing the fluid via a syringe, and the dermis can then be allowed to lay back down and heal.

As shown in FIG. 7B, a variation of device 10 adds a laser 31, such as a QSRL, to the device, that applies laser light 33 (e.g., a laser treatment) to a location on the skin and thereafter or simultaneously applies the magnetic field 16 to the same location. In some embodiments, the laser 31 comprises a fiber optic cable 32 that delivers the laser light 33 to the location. In some embodiments, this device can include a programmable controller that allows the user to set the strength, intensity, and/or duration of the laser and/or magnetic field applied to the skin, e.g., to vary the magnetic field temporally and/or spatially, or to vary the wavelength of the laser treatment.

Temporary Magnetic Body Art

In another aspect, the invention provides methods of decorating the body, e.g., any part of the body. Once a magnetic ink tissue marking has been created, magnetic decorative items can be attached. For example, an area of the body, e.g., the arm, earlobe, forehead, navel, or ankle, is tattooed using the magnetic ink described herein. Once the tattoo has healed, decorative items attached to small, strong magnets (e.g., about 0.5 Tesla, 1 Tesla, 1.5 Tesla, 2 Tesla, or more) can be temporarily adhered to the skin.

In some embodiments, the decorative item is an item of jewelry. In some embodiments, the decorative item is made to look like, e.g., an animal, an insect, a flower, or a leaf. In some embodiments, the decorative item is made to look like an unnatural body part, e.g., an extra eye or a horn. In some embodiments, the magnetic ink comprises particles coated with a chromophore so as to make the tattoo practically invisible to the naked eye, so that it is not generally visible, but provides a location to hold magnetic items. Thus, the invention also includes methods of creating an attachment site for magnetic items, by implanting a sufficient amount of magnetic ink, e.g., the magnetic ink described herein, sub-dermally to create an area of "magnetic skin," which has a sufficient attraction to or for a magnetic decorative item to hold the decorative item in place, but allows the decorative item to be removed painlessly. The invention also includes decorative magnetic items suitable for use as temporary magnetic body decoration or body art.

EXAMPLES

The invention is further described in the following examples, which do not limit the scope of the invention described in the claims.

Example 1

Magnetite Tissue Markings

Described herein is a small animal study of a novel magnetic "ink" and removal methods. Magnetite ($Fe_3O_4$, Pea Ridge Iron Ore Company, Inc.; item code M-25; Sullivan, Mo.) particles, 1.4 µm in diameter were mixed in glycerin (20% w/w), which provides sufficient viscosity for a suspension. The particle size was chosen to be within the 0.5 to 4 µm range typical for skin tattoos (Taylor et al., J. Invest. Dermatol., 97:131-136 (1991)). The suspension was used to make magnetite tattoos. A standard oscillating tattoo machine with needle array for commercial tattooing was used (Spaulding and Rogers, Albany, N.Y.), set to a puncture depth of approximately 1 mm. Fifteen hairless, albino rats were used for the study. The animals were anesthetized by a combination of ketamine, 45-75 mg/kg and xylazine 10-20 mg/kg, given intramuscularly. A total of 72 tattoos, each 1×3 cm, were made on the backs of the rats, and allowed to mature for 4 months before any treatment was done.

Photographic Analysis: A Nikon Digital camera (Nikon Digital, Channel RGB, E950, 6V, 0.8 A NTSC, Japan) was used to take pictures before laser treatment, one hour after treatment, 1 week post treatment, 2 weeks post treatment and 3 weeks post treatment. As a measure of relative lightening or darkening, a pixel histogram analysis (Corel Photo Paint 8, Channel RGB, Windows NT) was performed from the digital images. Relative lightening or darkening was measured by the mean pixel value in photographs within the region of interest (ROI) defined by the tattooed area of skin. Pixel values ranged from 0-255 because of the standard 8-bit digitization, with 0 being the maximum dark value and 255 being the maximum bright value. Pixel values were used for statistical analysis (see below).

Histologic analysis: 6 mm punch biopsies were obtained from treated and control sites at the following time points: before treatment; one hour post treatment; one week post treatment; 2 weeks post treatment; and 3 weeks post treatment. The biopsy wounds were closed with 4-0 silk sutures, which were removed after one week. Biopsy samples were immediately fixed in 10% formalin, then processed routinely and embedded in paraffin. Vertical sections were obtained and stained lightly with eosin, in order to easily see the magnetite tattoo ink particles. Standard hematoxylin and eosin staining of sections was also performed. The sections were blindly analyzed by three histopathologists for the following features: amount of ink in the papillary dermis on a scale of 0-5, with 5 being a maximum; and the presence of alignment and vertical streaking patterns of magnetite particles on a scale of 0-5, with 0 being no streaking and 5 being the most obvious streaking pattern.

Statistical analysis: Measures included the pixel values from each tattoo image, ratings of ink in the papillary dermis, and ratings of vertical streaking pattern in the papillary dermis. The mean, standard deviation and median of pixel values for each treatment condition were calculated. To compare the non-parametric data, Kruskal-Wallis tests were used. After Kruskal-Wallis tests, a post-hoc Mann-Whitney test was performed, and the global p value was corrected by Bonferroni test ($p<0.05$).

Results

Figure 2:
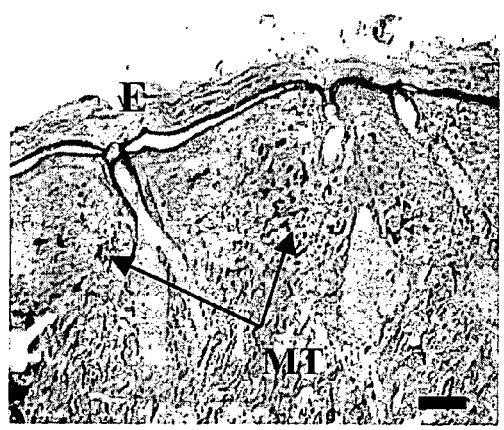
FIG. 2 is a photomicrograph showing the histological appearance of a 4 month old magnetite ink tattoo. There is a predominance of ink (arrows) in the middle and deep reticular dermis, without a streaking pattern. Scale bar 100 um, 4×, eosin stained. MT, magnetite tattoo ink. E, epidermis.
Figure 5:
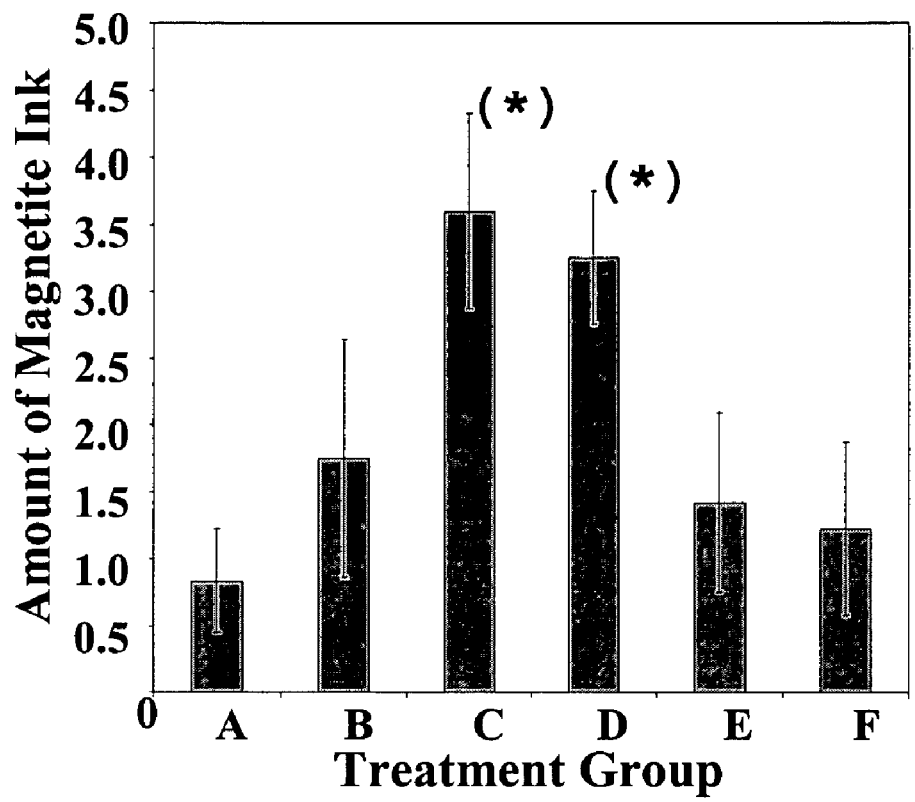
FIG. 5 is a bar graph illustrating the amount of tattoo ink in the papillary dermis. Tattoos treated with QSRL and magnets had significantly greater ink in the papillary dermis (*).
Figure 6:
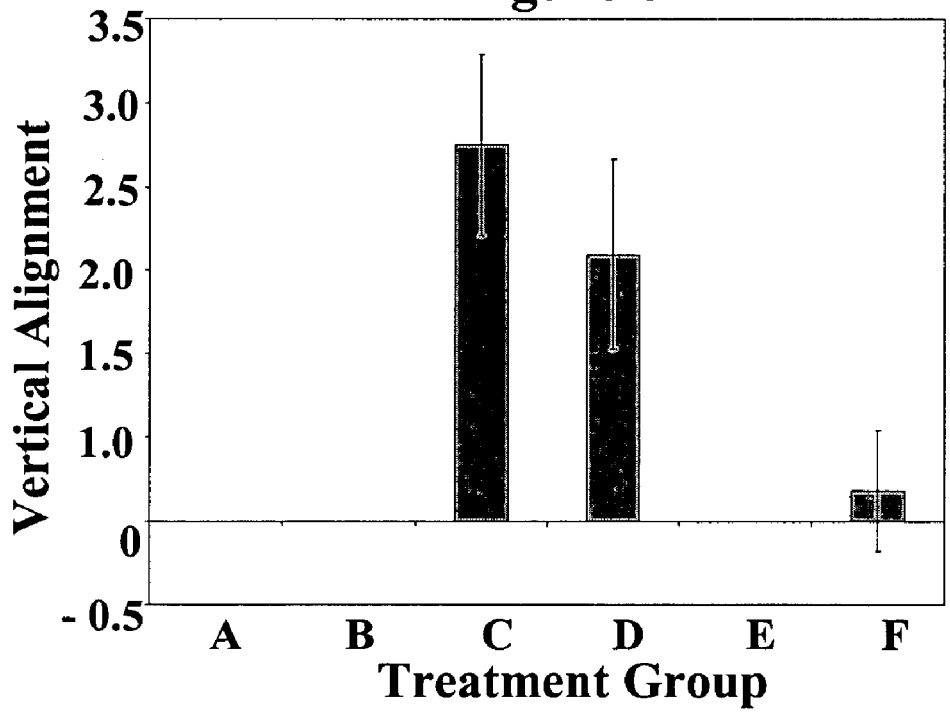
FIG. 6 is a bar graph illustrating the degree of vertical streaking pattern. Application of magnets after QSRL causes streaking pattern in the dermis, apparently along magnetic field lines. Key for FIGS. 5 & 6: A, Tattoos alone; B, one hour post QSRL alone; C, one hour post QSRL and magnet; D, 3 weeks post QSRL and magnet; E, 3 weeks post QSRL alone; F, one hour post magnet alone.

The magnetite made dark black or blue-black skin tattoos, which healed easily and were stable. No evidence of inflammation or scarring was noted at a four month follow-up after making the magnetite tattoos. The average brightness, as determined by pixel value of untreated tattoos, was 97 out of 255 (FIG. 1A). Histological analysis showed ink predominantly in the mid to deep reticular dermis, where the ink particles were in small clusters without any particular alignment (FIG. 2). The results of the statistical analysis of the amount of tattoo ink in the papillary dermis are shown in FIG. 5; results of statistical analysis of vertical alignment and streaking are shown in FIG. 6.

Example 2

Removal of Magnetite Tissue Markings

A Q-switched ruby laser (QSRL) and permanent magnets were investigated as agents for potentially clearing the tattoos, alone and in combination.

The tattoos were divided into six groups. Twelve tattoos per group were studied grossly and histologically after the following manipulations: tattoos alone (no treatment, control; Group A in FIGS. 5 and 6); 1 hour post QSRL alone (Group B); 1 hour post QSRL and magnet (Group C); 3-weeks post QSRL alone (Group E); 3-weeks post QSRL and magnet applied for 3 weeks (Group D); short-term (1 hour) application of magnet alone (Group F). The QSRL (Spectrum RD1100; Palomar Medical Products Inc., Burlington Mass.) had a nominal pulse duration of 30 nsec and wavelength of 694 nm. Treatment exposure fluence was 4.5 $J/cm^2$ with a 6.5 mm spot size, and partial overlapping of the pulses to avoid skipping areas of treatment. Permanent magnets of 1.4 Tesla (Neodymium alloy, a gift from J. Dallarosa, Coherent Inc., Santa Clara, Calif.) 600 mg and 6 mm diameter were used, applied to the skin surface overlying the tattoos alone and in combination with prior laser treatment. These are among the most powerful small permanent magnets which are readily available. A thin layer of tegaderm tape was applied between the magnet and the tattooed skin, to avoid direct contact of the skin with the magnet. Short-term application of magnets (one hour) was achieved by directly placing the magnet on the skin with tegaderm tape in between, while the animal was still anesthetized. Attractive force between the magnets and tattooed skin was easily perceived, and were sufficient to "stick" the magnets to the skin surface (FIG. 1C).

Figure 1B:
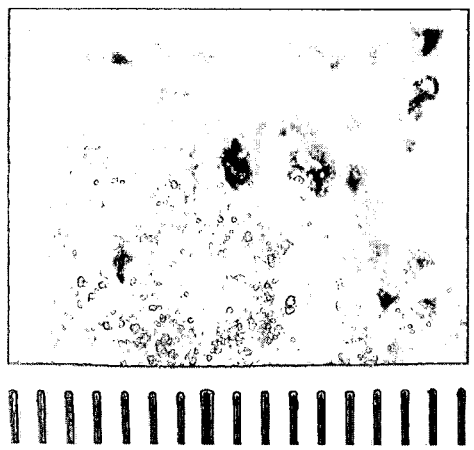
Figure 1C:
Figure 1D:
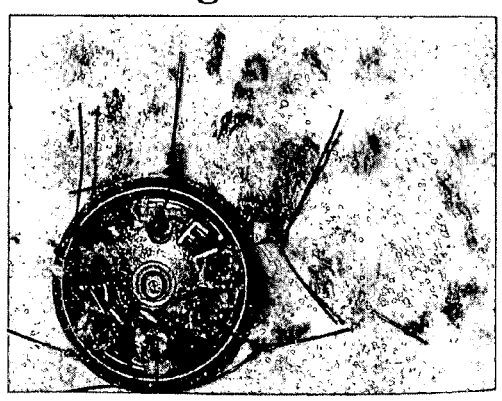

Long-term application of magnets (3 weeks) was achieved by adhering the magnet to a thin plastic disc 1 cm in diameter, and suturing the disc to the skin surrounding the magnetite tattoo (FIG. 1D). Wound care after placing tattoos and after laser treatment consisted of cleansing and daily application of bacitracin ointment for 7 days, after which any epidermal injury had healed.

Results: Short Term Application of Magnets Alone

Figure 3A:
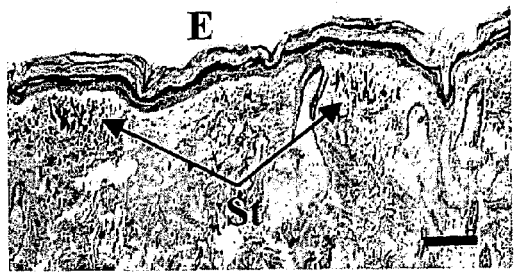
FIGS. 3A-3D are photomicrographs showing the histological appearance of tattoos treated with QSRL and magnets. 3A, mature magnetite ink tattoo treated with magnets alone. 3B, one hour after QSRL treatment followed by magnet application, showing increased ink in the papillary dermis under an intact epidermis. 3C, one hour post QSRL treatment followed by magnet application without an intact epidermis. 3D, three weeks post QSRL treatment, with magnet application for three weeks. Ink is significantly retained in the papillary dermis close to the dermo-epidermal junction (DEJ), compared with controls. Eosin stain, scale bar 100 um, 4×. E, epidermis; St, streaking.

Magnets applied for one hour did not significantly affect tattoo brightness ($p=0.285$) compared to untreated tattoos. Biopsies taken one hour after the application of magnets on mature tattoos without laser treatment, revealed no significant change in particle distribution ($p=0.133$) compared with untreated stable tattoos. FIG. 3A shows a mature magnetite ink tattoo treated with magnets alone. There is no significant difference in the amount and distribution of ink compared to FIG. 2, however some streaking characteristic of magnet application is seen (arrows).

In 4 out of 12 biopsy samples, magnets produced a minor degree of vertical streaking pattern, which was not statistically different from untreated tattoos (p=0.071; see FIG. 6).

Results: Short Term Application of Magnets Post QSRL Treatment

Figure 3B:
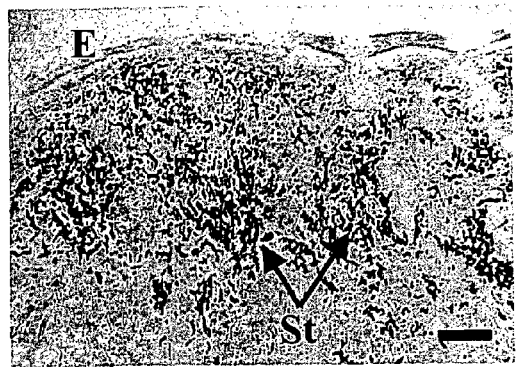
Figure 3C:

Immediate whitening of the area was seen upon treatment with QSRL (FIG. 1B). However, in small areas of the tattoos, QSRL treatment caused local epidermal damage, e.g., epidermal erosions with a small amount of blood or serous fluid appearing at the skin surface. External application of magnets for 1 hour following a QSRL treatment, did not significantly affect the brightness of tattoos (p=0.33) compared with laser alone. At sites with epidermal damage, magnetite ink particles were extracted (removed) from the skin by magnet application. This was evident by the appearance of ink on the under surface of the tegaderm tape, which occurred only where the magnet was applied. Epidermal damage was necessary for ink to be extracted by magnets. Histologically, magnet application for 1 hour after QSRL caused a significant upward migration of magnetite ink in the papillary dermis. Compared with control, there was a predominance of ink particles in the papillary dermis (p<0.0001; FIG. 5) at or close to the dermo-epidermal junction in 11 out of 12 samples (FIG. 3B). Coarse dermal spaces similar to those previously described after QSRL treatment of tattoos (Taylor et al., *J. Invest. Dermatol.*, 97:131-136 (1991)), and a sparse dermal infiltrate were also present. Areas with epidermal damage showed ink extending to the surface of the skin (FIG. 3C). A characteristic vertical streaking pattern of the ink particles was seen in the dermis only after magnet application, apparently along magnetic field lines. FIG. 3B shows a mature tattoo one hour after QSRL treatment followed by magnet application, showing increased ink in the papillary dermis under an intact epidermis. FIG. 3C shows a tattoo one hour post QSRL treatment followed by magnet application without an intact epidermis. The ink particles are streaked and extend to the tissue surface. This streaking pattern was not seen in the tattoos treated with laser alone (p<0.0001; FIG. 6).

Results: QSRL Treatment Alone

Figure 4A:
FIGS. 4A-4B are photomicrographs showing the histological appearance of tattoos treated with QSRL alone. 4A, one hour post QSRL treatment, ink particles are dispersed throughout the reticular dermis and there is no streaking pattern. 4B, three weeks post QSRL treatment, there is significant clearing of ink from the papillary and reticular dermis. Eosin stain, scale bar 100 μm, 4×. E, epidermis.
Figure 4B:
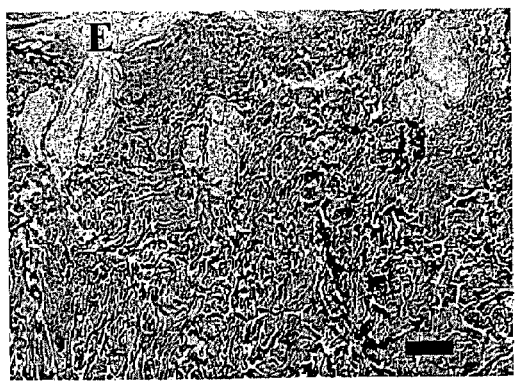

One hour after QSRL treatment of tattoos, there was cellular debris but no magnetite particles on the under surface of the tegaderm tape. Biopsies revealed predominance of ink particles mostly in the reticular dermis with obvious focal disruptions of dermis and epidermis, and an inflammatory infiltrate (FIG. 4A). Laser treatment caused local dispersion of ink clusters compared with the untreated tattoos, but unlike sites after magnet application there was no streaking pattern or vertical alignment of the particles. Three weeks after QSRL treatment alone, tattoos appeared lighter than the controls. However, by statistical analysis of the pixel values the lightening was not significant (p=0.214). Complete healing of the treated area was seen, without any evidence of scarring, infection, granulation tissue formation or skin textural changes. Biopsies taken 3 weeks after QSRL treatment, showed distribution of the ink particles throughout the reticular dermis similar to untreated tattoos. No streaking pattern was seen (FIGS. 4B, 6).

Results: Long Term Application of Magnets Post OSRL Treatment

Figure 3D:

Application of magnets for 3 weeks after laser treatment, caused significant darkening of the tattoo under the magnet (p<0.0001), compared to tattoos treated with laser alone. No particles were detected on the under surface of the magnet. Histological analysis showed ink predominance in the papillary dermis and close to the dermo-epidermal junction in 10 out of 12 samples, with some vertical streaking pattern (FIGS. 3D, 6). Consistent with the gross appearance of healing without scar, there was no residual inflammation or fibrosis.

CONCLUSIONS

Magnetic ink can be successfully used to make tissue markings, and these tissue markings can be grossly and microscopically manipulated in vivo by external magnetic fields. Furthermore, the application of a QSRL treatment followed by application of an external magnetic field produced a synergistic effect, resulting in even more efficient alteration of the magnetic ink tissue marking.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A magnetic tattoo ink composition comprising magnetic particles, wherein the magnetic particles are from 1.0 to 5 μm in diameter, and vary in diameter by less than a factor of about two, and wherein the composition is sterile, wherein the magnetic particles are coated with a chromophore of a color other than black.

2. The magnetic tattoo ink composition of claim 1, wherein the magnetic particles comprise magnetite ($Fe_3O_4$).

3. The magnetic tattoo ink of claim 1, further comprising a carrier.

4. The magnetic tattoo ink of claim 3, wherein the carder is selected from the group consisting of ethanol, purified water, witch hazel, antiseptic mouthwash, propylene glycol, glycerol, denatured alcohols, methanol, isopropyl alcohol, ethylene glycol, formaldehyde, glutaraldehyde, surfactants, and detergents.

5. The magnetic tattoo ink compositions of claim 1, wherein the magnetic particles further comprise a polymer.

6. The magnetic tattoo ink composition of claim 1, wherein the particles further comprise a chromophore.

7. The magnetic tattoo ink composition of claim 1, comprising magnetic particles of one color and non-magnetic particles of another color.

8. The magnetic tattoo ink composition of claim 7, wherein the magnetic particles are blue and the non-magnetic particles are yellow.

9. The magnetic tattoo ink composition of claim 7, wherein the magnetic particles are yellow and the non-magnetic particles are blue.

10. A method of making a magnetic tattoo ink tissue marking, the method comprising
obtaining a magnetic tattoo ink composition of claim 1, and
implanting the magnetic tattoo ink composition into the tissue.

11. The method of claim 10, comprising implanting the magnetic tattoo ink composition to form a pattern.

12. The method of claim 11, wherein the pattern formed by the implanted magnetic tattoo ink composition is a name.

13. The method of claim 12, further comprising implanting a non-magnetic tattoo ink composition to form another pattern, thereby forming a design that includes both the magnetic and non-magnetic ink patterns.

14. The method of claim 13, wherein the magnetic tattoo ink composition and non-magnetic tattoo ink composition comprise different colors.

15. The method of claim 13, wherein the pattern formed by the implanted magnetic tattoo ink composition is a name.

16. The method of claim 15, wherein the pattern formed by the implanted non-magnetic tattoo ink composition is a background for the name.

17. A method of altering the appearance of a magnetic ink tissue marking comprising the magnetic tattoo ink composition of claim 1, the method comprising applying a magnetic field to the tissue sufficient to move the magnetic particles of the magnetic tattoo ink composition, to thereby alter the appearance of the tissue marking.

18. The method of claim 17, wherein the method further comprises applying a Q-switched ruby laser treatment before applying the magnetic field.

19. The method of claim 18, further comprising repeating either the application of a magnetic field, the application of a Q-switched ruby laser treatment, or both, to the tissue, until the magnetic ink has been removed from the tissue.

20. The method of claim 17, wherein the method further comprises removing a portion of the epidermis before or while applying the magnetic field.

21. The method of claim 20, wherein the magnetic field is applied to the tissue for a length of time sufficient to cause the magnetic ink tissue marking to appear darker.

22. The method of claim 13, wherein the magnetic field is applied to the tissue for a length of time sufficient to lighten or remove the magnetic ink from the tissue.

23. The method of claim 22, wherein the removal of the magnetic ink removes a pattern or a color.

24. The method of claim 23, wherein the pattern is a name.

25. A method of attaching a magnetic object to a portion of skin, the method comprising obtaining a magnetic tattoo ink composition of claim 1;
implanting the magnetic tattoo ink composition into the skin in a manner sufficient to create a magnetic area on the skin; and
attaching a magnetic object to the skin.

26. The method of claim 25, wherein the magnetic tattoo ink composition is substantially the same color as the skin.

27. A magnetic tattoo ink composition comprising magnetic particles, wherein the magnetic particles are from 1.0 to 5 μm in diameter, and vary in diameter by less than a factor of about two, wherein the magnetic particles further comprise a polymer and are coated with a chromophore of a color other than black, and wherein the composition is sterile.

28. The magnetic tattoo ink composition of claim 27, comprising magnetic particles of one color and non-magnetic particles of another color.

29. The magnetic tattoo ink composition of claim 27, wherein the magnetic particles comprise magnetite ($Fe_3O_4$).

30. The magnetic tattoo ink of claim 27, further comprising a carrier.

31. The magnetic tattoo ink of claim 30, wherein the carrier is selected from the group consisting of ethanol, purified water, witch hazel, antiseptic mouthwash, propylene glycol, glycerol, denatured alcohols, methanol, isopropyl alcohol, ethylene glycol, formaldehyde, glutaraldehyde, surfactants, and detergents.

32. A method of making a magnetic tattoo ink tissue marking, the method comprising
obtaining a magnetic tattoo ink composition of claim 27, and implanting the magnetic tattoo ink composition into the tissue.

33. A method of altering the appearance of a magnetic ink tissue marking comprising the magnetic tattoo ink composition of claim 27, the method comprising applying a magnetic field to the tissue sufficient to move the magnetic particles of the magnetic tattoo ink composition, to thereby alter the appearance of the tissue marking.

* * * * *